US005182152A

United States Patent [19]

Ericson

[11] Patent Number: 5,182,152

[45] Date of Patent: Jan. 26, 1993

[54] LABEL DISPENSING SHEET

[76] Inventor: Thomas H. Ericson, 1733 S. 5th St., Milwaukee, Wis. 53204

[21] Appl. No.: 628,618

[22] Filed: Dec. 17, 1990

Related U.S. Application Data

[62] Division of Ser. No. 397,772, Aug. 23, 1989, Pat. No. 4,978,143.

[51] Int. Cl.⁵ ........................ A61F 13/02

[52] U.S. Cl. ........................ 428/42; 428/40; 428/43; 428/136; 428/195; 428/204; 428/207; 428/213; 428/215; 428/217; 283/36; 283/81; 283/101; 283/103; 283/105; 40/641; 40/27; 40/299; 40/360; 40/638

[58] Field of Search ........................ 428/40, 42, 43, 136, 428/195, 204, 207, 216, 213, 215; 283/36, 37, 38, 41, 42, 43, 81, 101, 103, 105; 40/641, 27, 299, 359, 360, 638, 661

[56] References Cited

U.S. PATENT DOCUMENTS

| | | | |
|---|---|---|---|
| 2,679,928 | 6/1954 | Bishop, Jr. et al. | 206/56 |
| 2,883,044 | 4/1959 | Kendrick | 206/56 |
| 2,893,144 | 7/1959 | Cunningham | 40/641 |
| 3,070,482 | 12/1962 | Cunningham | 156/269 |
| 3,191,767 | 6/1925 | Glowiak | 40/461 |
| 3,463,515 | 8/1969 | Thompson | 283/37 |
| 3,561,147 | 2/1971 | Valencia | 40/360 |
| 3,566,522 | 3/1971 | Leach et al. | 40/641 |
| 3,795,982 | 3/1974 | Cunningham | 33/111 |
| 3,805,426 | 4/1974 | Cunningham | 40/2 R |
| 3,857,587 | 12/1974 | Friedman | 283/42 |
| 3,877,576 | 4/1975 | Kishi | 428/43 |
| 3,877,729 | 4/1975 | Friedman | 283/42 |
| 3,924,744 | 12/1975 | Heimann | 40/461 |
| 3,937,493 | 2/1976 | Fasbender | 283/41 |
| 3,958,816 | 5/1976 | Remmey, III | 283/38 |
| 3,995,389 | 12/1976 | Mathis | 283/42 |
| 4,004,362 | 1/1977 | Barbieri | 428/43 |
| 4,019,759 | 4/1977 | Stanton | 283/42 |
| 4,175,777 | 11/1979 | Horn | 283/42 |
| 4,201,403 | 5/1980 | Turner | 283/21 |
| 4,291,900 | 9/1981 | Feng | 281/15 R |
| 4,422,672 | 12/1983 | Levi | 283/39 |
| 4,520,055 | 5/1985 | Jeter | 428/55 |
| 4,544,182 | 10/1985 | Spring | 283/42 |
| 4,584,219 | 4/1986 | Baartmans | 428/43 |

*Primary Examiner*—Ellis P. Robinson
*Assistant Examiner*—Nasser Ahmad
*Attorney, Agent, or Firm*—Foley & Lardner

[57] ABSTRACT

A label dispensing sheet includes a backing sheet having a layer of a pressure sensitive adhesive releasing material on one face and having a weakened line across its width, a row of adhesive labels releasably disposed on the backing sheet overlying the weakened line, and a release strip releasably disposed on the backing overlying the weakened line. The release strip has a weakened line at a position offset from the weakened line in the backing. This permits a user to grasp and pull away the release strip, exposing the ends of the labels for easy removal. The labels may, for example, be thin, plastic index tabs for labelling book pages.

13 Claims, 5 Drawing Sheets

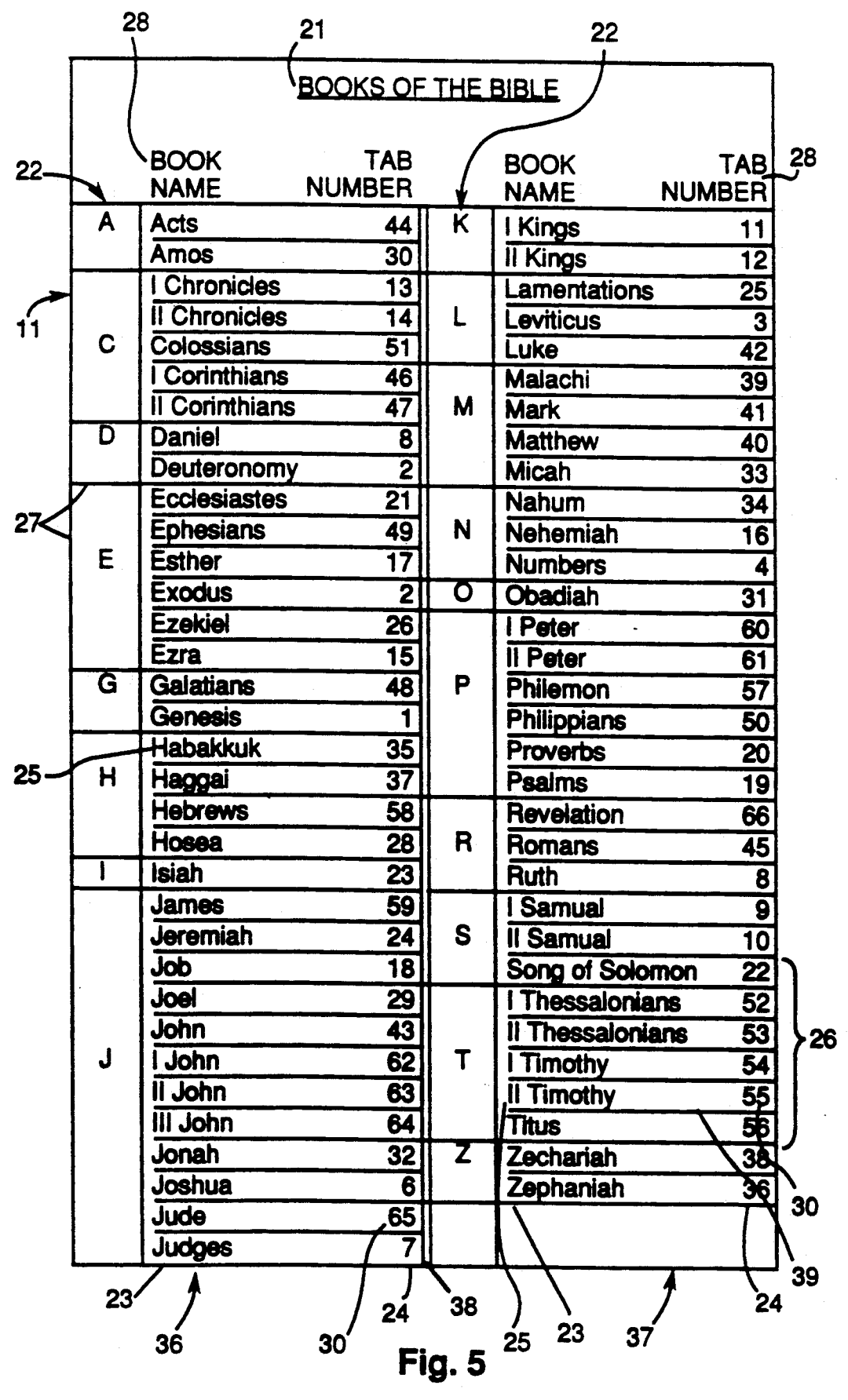

BOOKS OF THE BIBLE

| | BOOK NAME | TAB NUMBER |
|---|---|---|
| A | Acts | 44 |
| | Amos | 30 |
| C | I Chronicles | 13 |
| | II Chronicles | 14 |
| | Colossians | 51 |
| | I Corinthians | 46 |
| | II Corinthians | 47 |
| D | Daniel | 8 |
| | Deuteronomy | 2 |
| E | Ecclesiastes | 21 |
| | Ephesians | 49 |
| | Esther | 17 |
| | Exodus | 2 |
| | Ezekiel | 26 |
| | Ezra | 15 |
| G | Galatians | 48 |
| | Genesis | 1 |
| H | Habakkuk | 35 |
| | Haggai | 37 |
| | Hebrews | 58 |
| | Hosea | 28 |
| I | Isiah | 23 |
| J | James | 59 |
| | Jeremiah | 24 |
| | Job | 18 |
| | Joel | 29 |
| | John | 43 |
| | I John | 62 |
| | II John | 63 |
| | III John | 64 |
| | Jonah | 32 |
| | Joshua | 6 |
| | Jude | 65 |
| | Judges | 7 |

| | BOOK NAME | TAB NUMBER |
|---|---|---|
| K | I Kings | 11 |
| | II Kings | 12 |
| L | Lamentations | 25 |
| | Leviticus | 3 |
| | Luke | 42 |
| M | Malachi | 39 |
| | Mark | 41 |
| | Matthew | 40 |
| | Micah | 33 |
| N | Nahum | 34 |
| | Nehemiah | 16 |
| | Numbers | 4 |
| O | Obadiah | 31 |
| P | I Peter | 60 |
| | II Peter | 61 |
| | Philemon | 57 |
| | Philippians | 50 |
| | Proverbs | 20 |
| | Psalms | 19 |
| R | Revelation | 66 |
| | Romans | 45 |
| | Ruth | 8 |
| S | I Samual | 9 |
| | II Samual | 10 |
| | Song of Solomon | 22 |
| T | I Thessalonians | 52 |
| | II Thessalonians | 53 |
| | I Timothy | 54 |
| | II Timothy | 55 |
| | Titus | 56 |
| Z | Zechariah | 38 |
| | Zephaniah | 36 |

Fig. 5

LABEL DISPENSING SHEET

This is a division of Ser. No. 397,772, filed on Aug. 23, 1989, now U.S. Pat. No. 4,978,143.

TECHNICAL FIELD

This invention relates to a system for providing a book having a series of distinct parts with index tabs which allow fast access to such parts, and a system for installing such index tabs.

BACKGROUND OF THE INVENTION

Books are usually subdivided into a series of chapters or similar parts which a reader may desire to individually reference. Where the chapters of such a book are titled as a sequence of numbers, e.g. Chapter 1, Chapter 2, etc., conventional tabs may be mounted at the outside margin of the page at the start of each such part to allow the reader to find that part quickly. Each tab bears a number corresponding to the number of the part or chapter marked. The tabs are commonly set in rows along the outside edge of the book, with each successive tab set beneath and to one side of the preceding tab.

Problems arise using such tabs with large books in which the chapters or parts have names or titles which are commonly referred to by readers in lieu of numbers. One such book is the bible, which in its Protestant version has 66 parts (called books) and in its Catholic version has 73 books. Numbering these books in sequence from 1-66 or 1-73 is of little help because few readers can remember which book has which number, and the reference system in common use for the bible utilizes the names of the books, together with chapter and verse, for example, II Timothy 2:15.

A variety of bible indexing systems have been used to improve ease of reference to the bible. Such systems generally include a series of adhesive tabs which can be secured to the outer margin of the page corresponding to the start of each book of the bible. Each tab has the appropriate book name on it, in full or abbreviated form. This allows the user to turn to the desired book after scanning the row of tabs to find the right name. Such indexing systems are useful, but still require the user to scan a series of names or titles to find the desired title. Moreover, the book names on the tabs are not in any systematic order, such as alphabetical order. Presently available bible indexing systems are thus of limited usefulness.

The tabs used in known bible indexing systems also have certain drawbacks. The pages of very large books such as the bible tend to be quite thin. Ordinary tabs when mounted on such pages are likely to cause the page to tear upon repeated use. Installation of such tabs is also difficult. The tabs are mounted initially on a peel-off backing sheet. The user must start the peel-off operation manually by picking at the sheet until the backing starts to separate from the tab label. This is a tedious and cumbersome process.

The user must then install the tabs in orderly rows. Present bible indexing systems provide no means for laying out and spacing the tabs, or provide a measuring strip which is little more than an ordinary ruler, and is only a fraction of the total length of all of the rows of tabs. It is most convenient to install the tabs in reverse order, starting with the last tab near the end of the book and working forward. Using conventional bible indexing systems, it is difficult to install the tabs in this manner and still ensure that the first tab will appear near the upper top corner of the book One system for addressing this type of problem involves providing the release paper backing of a tab sheet with a marginal scale for ensuring accurate manual placement of the tabs. See, for example, Cunningham U.S. Pat. No. 3,795,982, issued Mar. 12, 1974. This system involves the use of a long tab strip, which may become inconvenient when the number of tabs becomes large.

The table of contents in a bible frequently provides a list of the books of the bible in alphabetical order, together with the starting page number for that book. The table of contents might also include a reference to the number of chapters within the book, and an indication of whether the book is in the New Testament or the Old Testament. This type of index, while useful, still requires the reader to page through the book looking for the page number.

Various indexing systems have been proposed for books generally. Some such systems involve the use of built-in index dividers, in the form of recesses in page edges, projections which extend beyond the outer margin of a page, or tabs which clip onto a page. See, for example, Valencia U.S. Pat. No. 3,561,147, issued Feb. 9, 1971, Friedman U.S. Pat. No. 3,857,587, issued Dec. 31, 1974, Friedman U.S. Pat. No. 3,858,909, issued Jan. 7, 1975, Friedman U.S. Pat. No. 3,877,729, issued Apr. 15, 1975, Mathis U.S. Pat. No. 3,995,389, issued Dec. 7, 1976, and Feng U.S. Pat. No. 4,291,900, issued Sep. 29, 1981. Systems have also been proposed wherein a series of adhesively mountable tabs or markers having indicia such as numbers or colors are provided together with an adhesive backed index page which can be permanently mounted in the book. The index page includes a series of numbered blanks in which the reader is intended to write down the subject matter to be marked by the tab. Horn U.S. Pat. No. 4,175,777 issued Nov. 27, 1979, and Remmey, III U.S. Pat. No. 3,958,816 issued May 25, 1976 exemplify such systems.

Index tabs have been constructed in many different ways. Most such tabs suitable for use in book indexing systems include a portion which folds over a page edge and a portion coated with an adhesive for permanently securing the tab to the page. See, for example, Turner U.S. Pat. No. 4,201,403, issued May 6, 1980, Levi U.S. Pat. No. 4,422,672, issued Dec. 27, 1983, Cunningham U.S. Pat. No. 2,893,144, issued Jul. 7, 1959, Cunningham U.S. Pat. No. 3,070,482, issued Dec. 25, 1962, Cunningham U.S. Pat. No. 3,348,324, issued Oct. 24, 1967, Stanton U.S. Pat. No. 4,019,759, issued Apr. 26, 1977, and Leach U.S. Pat. No. 3,566,522, issued Mar. 2, 1971. A disc-shaped, adhesively backed transparent tab having identifying matter thereon has also been proposed. See, e.g. Thompson U.S. Pat. No. 3,463,515, issued Aug. 26, 1969. Laminated tabs having successive layers of flexible film, adhesive, face stock, and a second adhesive are also known. See, for example, Jeter U.S. Pat. No. 4,520,055, issued May 28, 1985.

Adhesive tabs or labels are frequently manufactured in rows on sheets of release paper backing. See, e.g., Cunningham U.S. Pat. No. 3,805,426 issued Apr. 23, 1974. To facilitate removal of such tabs or labels, such sheets have been provided with slits in the backing near one end of the labels (see Kendrick U.S. Pat. No. 2,883,044 issued Apr. 21, 1959) or with cuts that define stripping tabs (see, e.g. Bishop U.S. Pat. No. 2,679,928 issued Jun. 1, 1954.) These means for aiding peeling off the labels may not always provide for easy, selective removal of one label at a time, as may be needed when applying adhesive tabs to a bible.

The present invention addresses the foregoing problems with known indexing systems and provides an improved book indexing system which is especially suitable for providing a tabbed, indexed bible.

SUMMARY OF THE INVENTION

An indexing system according to the invention includes a table having a first series comprising words thereon arranged in alphabetical order, and a second series comprising numbers aligned with each word of the first series. Such a table is used together with a plurality of tabs each having numbers thereon which correspond to the numbers in the second series. The tabs have suitable means for securing each tab to a surface of a plurality of items to be indexed, such as pages. The table correlates the numerically numbered tabs with the alphabetical word listing, which words are typically the names of chapters or other subdivisions of the book to be indexed. In preferred embodiments, the words in the first series are the names of the books of the bible, and the table is permanently mountable in the book for easy reference. The invention further provides an indexed book in which the foregoing index table and tabs are installed or provided, and a book indexing kit including such an index table, a tab dispensing sheet, and a measuring device for accurately laying out the tabs in the book.

According to another aspect of the invention, a convenient device for positioning index tabs is provided which comprises a sheet having an array of rows and columns thereon, which columns (or rows) can be separated from each other and reunited end-to-end to form an elongated layout strip which is used to ensure accurate manual placement of index tabs in a book such as the bible.

According to a further aspect of the invention, an improved resealable package for a retrofitable indexing system comprises a bag having an open end defining a mouth, a pair of first and second adhesive layers or zones disposed on an outer surface of the bag on opposite respective sides of the mouth, and a backing sheet having a folded end flap, the bag being disposed on the backing sheet such that the first adhesive layer secures the bag to the backing, and the flap is folded back over the mouth of the bag to releasably engage the second adhesive layer. In a preferred embodiment, the index positioning sheet described above is formed on the package backing.

According to an additional aspect of the invention, a label dispensing sheet is provided which includes a backing sheet having suitable means for releasing a pressure sensitive adhesive on a face thereof, i.e. a release surface, and having a weakened line across the width thereof. A row of labels each comprising a base layer having a layer of pressure sensitive adhesive coated on a bottom face thereof and indicia disposed on a top face thereof are disposed in contact with the release face of the backing sheet, and a portion of each label overlies the weakened line. A release strip having a layer of adhesive on a bottom face thereof is also disposed in contact with the release face of the backing, overlying the weakened line, at one end of the row of labels. The release strip has a line of weakness extending in the widthwise direction thereof at a position offset from the weakened line in the backing sheet. The release strip provides a convenient means for starting peeling off of the backing so that the tabs may be individually removed from the sheet.

BRIEF DESCRIPTION OF THE DRAWING

The invention will be further described with reference to the accompanying drawing figures, wherein like numerals denote like elements, and:

FIG. 5 is a front view of an index table shown schematically in FIG. 1;

DETAILED DESCRIPTION OF PREFERRED EMBODIMENTS

Figure 1:
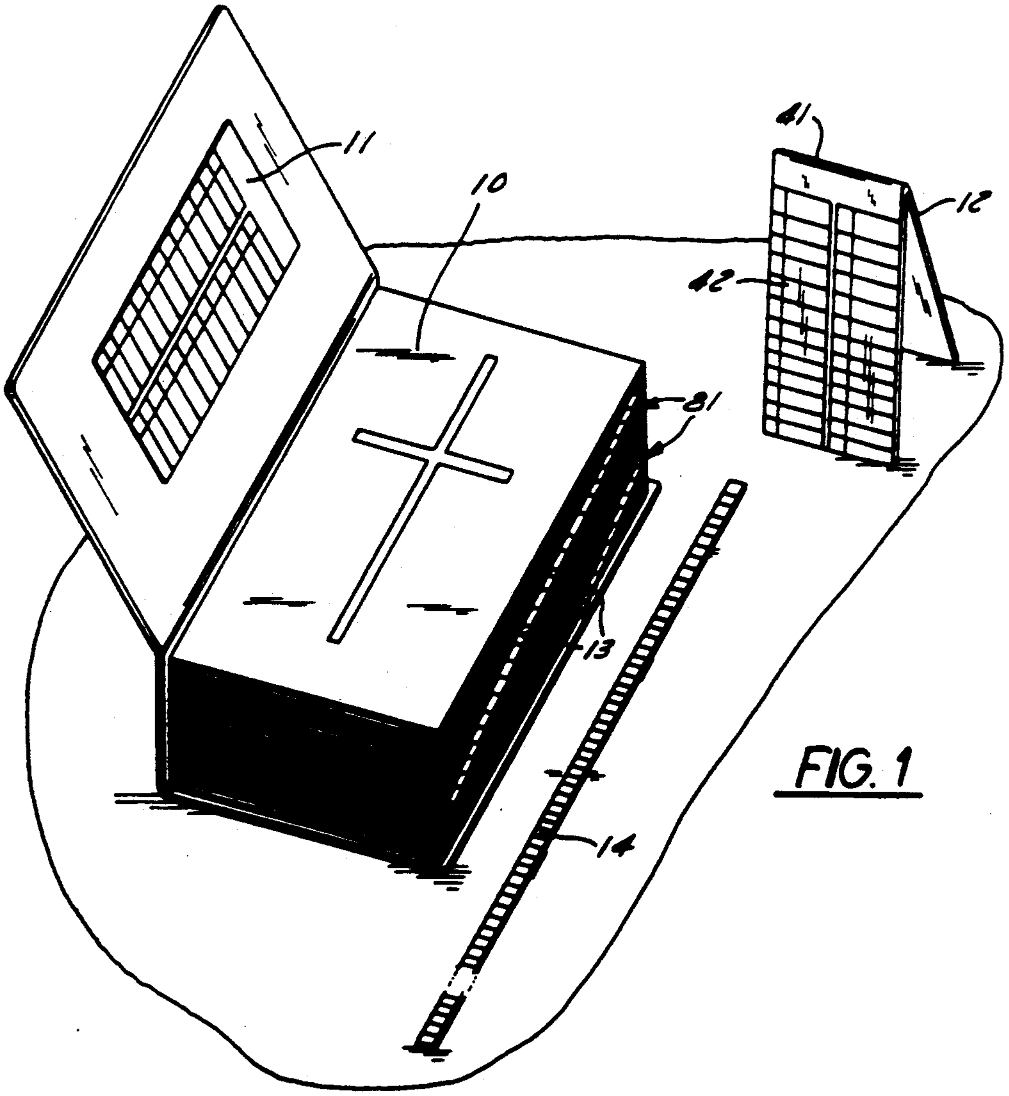
FIG. 1 is a perspective view of a book having the indexing system of the invention installed therein.

FIG. 1 illustrates a bible indexed according to the invention including a book (bible) 10, index table insert 11, index table stand-up chart 12, index tabs 13 and tab layout strip 14. Each of these components is described in detail hereafter.

As shown in FIG. 5, index table insert 13 comprises a sheet of paper, cardboard or similar material having suitable means for permanent attachment at a desired position within the book 10, for example inside the front cover as shown, on the back cover, or at any convenient location near the beginning or end of book 10. Index table insert 11 has a suitable printed heading (title) 21 describing the contents of the table, and a three series 22,23,24 in column form which facilitate rapid access to the bible. A central column 23 comprises a series of names for book subparts 25, i.e. chapters, biblical books, or the like, arranged in alphabetical order. Left column 22 comprises a series of large symbols which are aligned with like entries in central column 23. In the illustrated embodiment, left column 22 comprises letters of the alphabet, set in enhanced (e.g. enlarged or bold) type as compared with entries in central column 23, to allow the reader's eye to quickly spot a corresponding group 26 of entries in column 23 which start with the same letter. Horizontal and vertical boundary marks (lines) 27 set apart each group 23 for faster visual identification.

A right column 24 contains numbers 30 which correspond to the actual order in which books 25 appear in bible 10. In general, numbers 30 in column 24 are preferably whole numbers which range from 1 to a predetermined maximum number as determined by the book in question (e.g. 66 for the Protestant verison of the bible.)

These numbers appear in non-numerical order, in other words, not in any sequence of increasing or decreasing numbers. Index tabs 13 bear the same numbers, e.g. 1–66, but are set in rows in numerical order, as further described below. Column headings 28 appear at the top of columns 23,24 to identify each column.

Aligned columns 22,23,24 are preferably divided into right and left halves 36,37 positioned side by side on insert 11. A dividing mark (line) 38 having an enhanced visual appearance as compared to lines 27 (a double line, for example) separates column halves 36,37. In the illustated embodiment, half 36 covers books of the bible from A through J, and half 37 includes the remaining books K through Z. Optionally, horizontal dividing lines 39 may be positioned between each aligned pair of entries in columns 23,24 to facilitate reading the indicated tab number in right column 24 once the correct book in column 23 has been located.

Thus, a reader seeking a particular book of the bible, for example, II Timothy, first seeks the enhanced letter T in left column 22. This keys the reader's eye to the correct group 26 of word entries 25 beginning with the same letter and the corresponding numbers 30. The reader then scans alphabetically within group 26 until the desired name is located in central column 23. The reader then scans horizontally along dividing lines 39 to the correct number entry 30 in right column 24. Number 30 (in this example the number "55" represents II Timothy) identifies the tab 13 the reader should turn to in the bible to find the desired subpart 25, namely the second book of Timothy in this example.

Stand-up index card 12 comprises an elongated card of a relatively stiff material, e.g. heavy paper or cardboard, having a transverse central fold 41 which allows card 12 to stand upright on a tabletop, as shown in FIG. 1. A front face 42 of card 12 is identical to index card 11. Card 12 provides the reader with a portable index which may be more convenient than permanent index 11 in some situations. Card 12 can also be used as a bookmark if a stand-up index is not needed. Card 12 resists becoming lost because it can be folded over a dozen or so pages.

Figure 6:
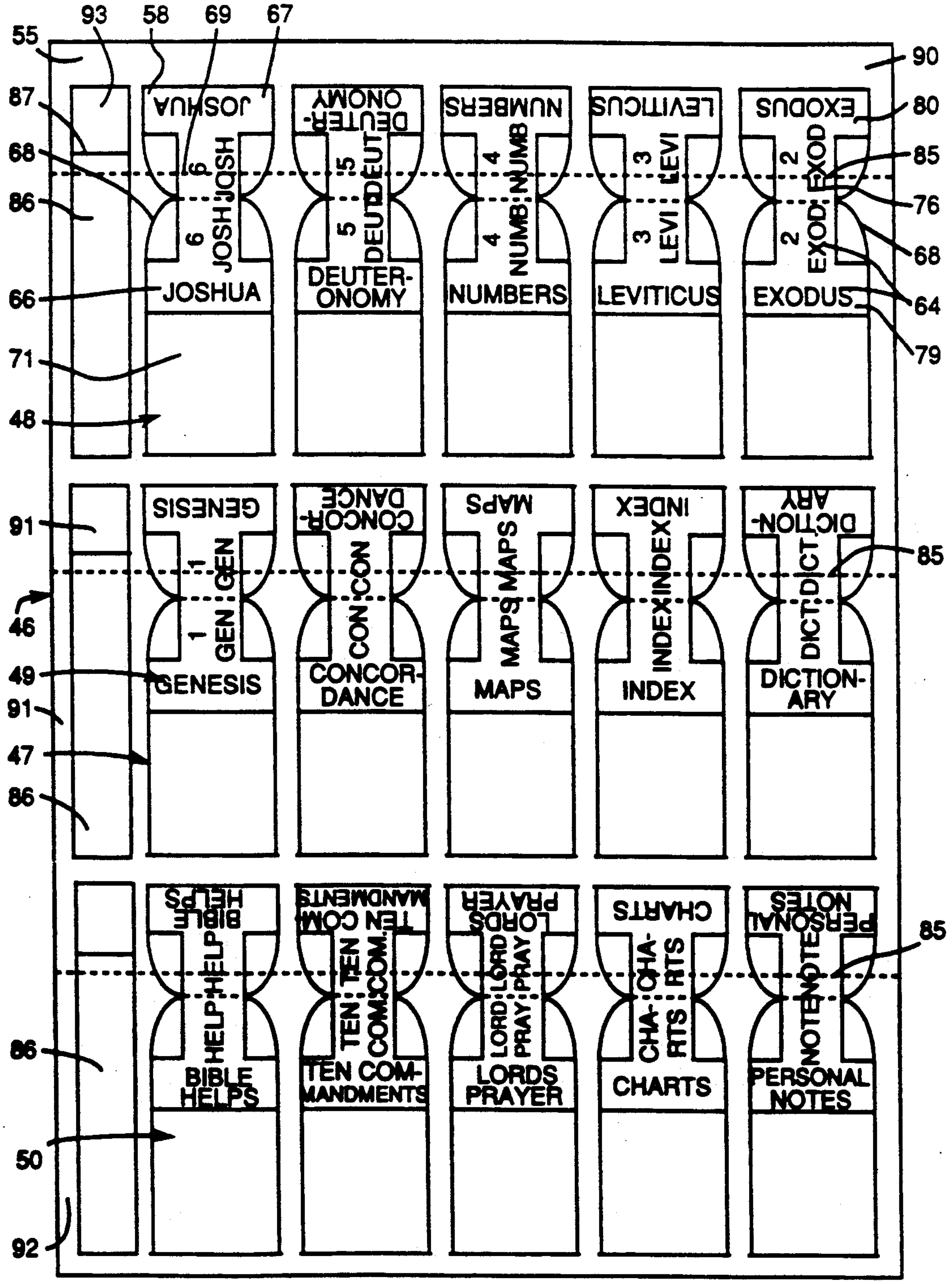
FIG. 6 is a plan view of a tab dispensing sheet according to the present invention.
Figure 7:
FIG. 7 is a partial sectional view taken along the line 7—7 in FIG. 6.

FIGS. 6 and 7 illustrate the construction of preferred tabs 13 for use in combination with permanent index 11 or portable index card 12. A tab dispensing sheet 46 has an array 47 of tabs 13 disposed thereon prior to installation of tabs 13 in book 10 to be indexed. As shown in FIG. 6, tab array 47 includes top, middle and bottom rows 48,49,50 of tabs 13. Each tab 13 of each row is aligned with corresponding tabs 13 in the other rows to define array 47.

Tab dispensing sheet 46 is a laminate formed on a release paper backing 55. A top face 56 of backing 55 is coated with a layer 54 of conventional pressure sensitive adhesive releasing material, such as silicone, so that tabs 13 may be peeled off of backing 55. As shown in FIG. 7, each tab 13 comprises a base layer 57A made of a flexible transparent film material, preferably a polyester film such as Mylar, a generally H-shaped intermediate layer 58 bearing desired indicia, and a covering layer 59 preferably identical to layer 57A. A layer of conventional pressure sensitive adhesive 60 is disposed on the entire underside of base layer 57A. Each of layers 57,59 preferably has a thickness in the range of about 1–2 mils (0.025–0.051 mm). Thinner layers 57,59 are desirable if feasible. The thickness of layers 57,59 is important. If these layers are too thin, tabs 13 will not have sufficient strength. If these layers are excessively thick, tabs 13, and particularly rounded transparent edge portions 73 described below, will become too stiff and tend to cause page tearing.

Intermediate layer 58 generally comprises a colored material which defines numbers corresponding to numbers 30 on index table 11. Intermediate layer 58 is preferably opaque, and includes a sublayer 63 of ink or pigment and readable indicia 64 disposed thereon. Sublayer 63 may be made of a gold metallic-colored ink, and indicia 64 may be made of conventional black ink printed thereon. Gold metallic ink normally tarnishes over time, but this drawback is prevented in the tabs according to the invention by plastic covering layer 59, which covers intermediate layer 58 and thereby prevents the gold ink from tarnishing. Indicia 64 include the tab number and optionally other information as described further below.

Each tab 13 comprises a front portion 66 and a rear portion 67 shorter in length than front portion 66. As shown in FIG. 6, front and rear portions 66,67 taper towards each other along rounded side edges 68 and meet at a transverse weakened fold line 69, at which tab 13 has its minimum thickness. Fold line 69 is preferably formed by etching away base layer 57A along this line so that tab 13 will tend to fold precisely along the weakened line 69. The part of front portion 66 that adjoins fold line 69 and mates with rear portion 67 has the same shape as rear portion 67 so that adhesive layer 60 will be entirely covered when tab 13 is folded and installed on a book page. Similarly, precise folding along line 69 is important because any exposed portion of adhesive layer 60 will tend to collect dust and dirt.

Figure 2:
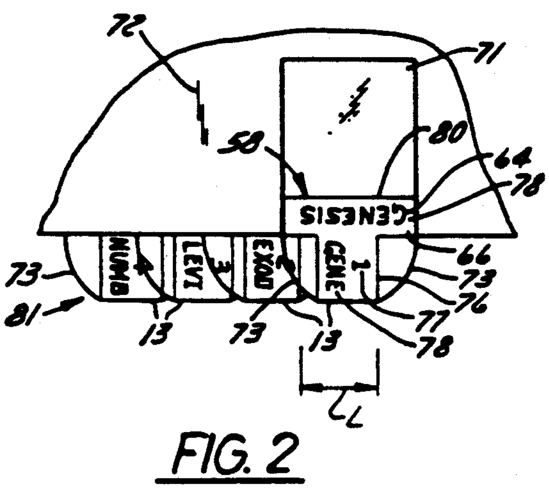
FIG. 2 is a top, partial view of the upper right corner of the indexed book shown in FIG. 1 with intervening pages above the first tab removed.

Referring to FIG. 2, front portion 66 of tab 13 has a reinforcing portion 71 that is secured directly against the outside margin of a book page 72. This reinforcing portion tends to prevent page 72 from tearing. Rounded edges 68 of front and rear portions 66,67 mate to define transparent, rounded side portions 73 of each tab 13 on opposite sides of H-shaped layer 58 as installed on a book page 72. Rounded portions 73 are of generally triangular shape, and preferably approximate a quarter-circle as shown. H-shaped layer 58 becomes T-shaped after tab 13 has been folded as shown in FIG. 2. The stem 76 thereof, which protrudes beyond the edge of page 72, includes indicia 64, namely the number 77 of the tab 13, and optionally an abbreviation 78 for the name of the book or chapter being referenced.

Indicia 64 preferably are printed twice on layer 58 so that indicia 64 appears on both sides of tab 13 when folded. Similarly, a crossbar portion 79 of layer 58, which is disposed at the page edge on both sides thereof, preferably includes the full name 80 of the book or chapter spelled out, as an additional indicia 64. If stress problems develop at portion 79, it may be desirable to lengthen stem 76 so that cross bar portion 79 is recessed (set back slightly) from the page edge.

Figure 3:
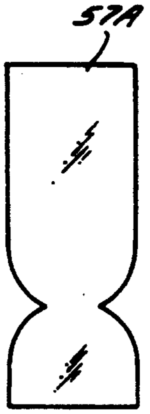
FIG. 3 is a plan view of a base layer of transparent plastic used as part of an index tab according to the invention.
Figure 4:
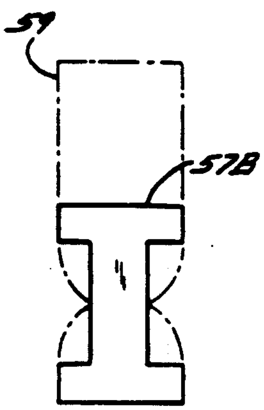
FIG. 4 is a plan view of a base layer of opaque paper used as part of an index tab according to an alternative embodiment of the invention.

FIG. 3 illustrates the shape of base layer 57A for each tab, with the other layers removed. FIG. 4 illustrates an alternative base layer 57B which is made of an opaque, flexible sheet material such as paper. Base layer 57B is generally H-shaped, i.e. the same shape as layer 58. When tab 13 is folded, side portions 73 comprise only covering layer 59, and thus have only half the thickness of the preceding embodiment utilizing base layer 57A. Where the thickness of the film used to make layer 59 is 2 mils, the overall thickness of side edge portions 73 decreases from 4 mils to 2 mils, greatly reducing the amount of expensive plastic film needed to make tabs 13. Side edge portions 73 are also rendered softer and more flexible due to the decrease in thickness.

Tabs 13 are installed in rows 81 with each successive tab below and to one side of the tab 13 above it. A new row 81 must be started when the tabs of the preceding row span essentially the entire length of book 10. The number of rows needed to index an entire book will depend on the size of the book and the tabs, and the number of parts to be indexed. Tabs 13 are preferably installed so that transparent rounded edge portions 73 overlie each other, with opaque, generally rectangular stem portions 76 of each successive tab being positioned adjacent to each other or slightly spaced apart, as shown in FIG. 2. This row configuration is advantageous because the overlapping tabs allow a greater number of tabs per row with no loss in tab strength or size. Rounded side edge portions 73 are transparent and thus do not obscure the stem portion(s) 76 of adjacent tabs 13.

Returning to FIG. 6, tab dispensing sheet 46 preferably includes an improved means for removing tabs 13 which may be advantageously employed for dispensing all kinds of adhesive labels. Release paper backing 55 has a plurality of parallel weakened lines, e.g. slits 85, which extend in the widthwise direction of tabs 13. One such slit 85 underlies each row 48,49,50 of tabs 13 beneath rear protion 67 of each tab 13, preferably proximal to but slightly spaced from fold line 69, i.e. underlying rounded side edges 68. At least about half of rear protion 67 of each tab 13 extends beyond slit 85, unlike in prior art sheets wherein only a small part of the label overlies the line.

A thin release strip 86 is disposed at one end of each row 48,49,50 near one side edge of sheet 46. Release strip 86 comprises a laminate essentially the same as each of tabs 13, including successive layers corresponding to adhesive layer 60, base layer 57A or 57B, a layer corresponding to intermediate layer 58 having instructions (e.g. "Hold Here") or other indicia thereon, and optionally a layer corresponding to covering layer 59. Strip 86 has a weakened line (slit) 87 therethrough which is close to but spaced apart from the associated underlying slit 85. Part of strip 86 thus overlies slit 85 and functions as an adhesive tape to prevent rupture of sheet 46 along each slit 85. Slit 87 is positioned on the same side of slit 85 as the large part of rear portion 67, that is, the part that extends over slit 85. Slit 85 is thus positioned between fold line 69 and slit 87, as shown in FIG. 6.

Slits 85 subdivide backing 55 into a narrow, elongated end segment 90 and a plurality of segments 91,92,93 of identical length but generally greater in width than end segment 90, as illustrated in FIG. 6. To remove tabs or labels 13 from sheet 46, the user begins by grasping a corner 94 of sheet 46 near slit 87 of the strip 86 aligned with the first row 48. By pulling back on corner 94, strip 86 separates at slit 87 and narrow end segment 90 of backing 55 starts tearing off along slit 85. As the user continues to pull end segment 90, part of the tab 13 adjacent to strip 86, namely the part overlying slit 85, becomes exposed, and that first tab 13 may then be easily grasped and peeled off from backing 55 without need for tediously grasping a small exposed edge. As tearing along slit 85 continues, the next tab 13 in first row 48 may be removed in a like manner, and so on until the tab remote from strip 86 has been removed. At this point end segment 90 is torn off completely and discarded.

The foregoing system allows one label to be removed at a time because the separable portion of the backing (end segment 90) is torn off at a right angle relative to the lengthwise direction of the tabs or labels 13, providing a zipper-like effect. This system also allows the user to remove some but not all labels from the row without releasing the remaining labels from the backing.

Referring to FIG. 6, once all tabs 13 in row 48 have been removed together with end segment 90, the process is repeated for the second row 49 by grasping the segment 91 of backing 55 which underlies rear portions 67 of tabs 13 in row 49 near slit 87 of the associated strip 86. Row 49 and the backing segment 91 underlying it are eventually removed, and the process is repeated for the final row 50 by removing segment 92. After the last tab 13 has been removed, the last segment 93 of backing 55 may be discarded.

The foregoing label dispensing sheet is particularly well adapted for the removal of preprinted, sequentially ordered labels such as bible tabs because the labels or tabs can be conveniently removed only in the correct order. In the embodiment shown in FIG. 6, tabs 13 are correctly ordered for installation in a Protestant (66 book) version of the bible. Additional unnumbered tabs 95 are included for indexing specific parts of the bible other than books, such as notes, maps, and the like. Several such sheets are typically provided in a bible indexing kit according to the invention to include all 66 or 73 books of the bible, each of like structure except for differences in indicia 64. In the alternative, a single large sheet 46 could also be employed. Such an enlarged sheet could be folded tranversely between rows 48,49,50 for packaging, as described hereafter.

Figure 10:
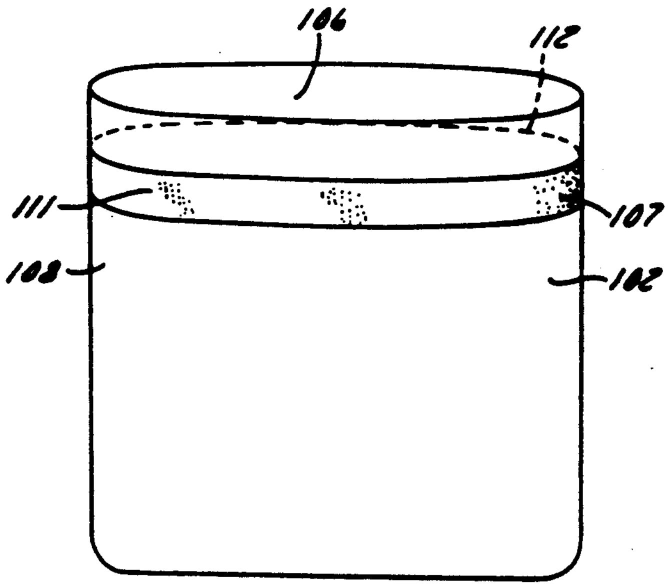
FIG. 10 is a perspective front view of a bag used in the the packaged indexing system shown in FIG. 8.

FIGS. 8 through 11 illustrate a packaged book indexing kit 100 according to the invention which comprises one or both of indexes 11 or 12, and one or more sheets 46 of tabs 13, which kit 100 is disposed in an improved resealable package 101. Package 101 comprises a clear plastic bag 102, e.g. made of polyethylene, and a relatively stiff backing 103, preferably made of heavy paper or cardboard. Bag 102 has a single open end which defines a mouth 106. A stripe 107 of releasable, pressure sensitive adhesive is disposed on front and back faces 108,109 of bag 102 in close proximity to mouth 106 so as to define a front adhesive layer 111 and a rear adhesive layer 112 for faces 108,109, respectively. Adhesive layers 111,112 are preferably positioned on the uppermost third of the bag as shown in FIG. 10.

The contents of kit 100 are placed inside bag 102 through mouth 106. Bag 102 is then positioned over a bottom end portion 113 of backing 103, and rear adhesive layer 112 is pressed against and secured to a medial portion of a front face 114 of backing 103. If desired, layer 112 may be made of permanent, nonreleasable adhesive so that bag 102 is permanently mounted on backing 103. However, if both adhesive layers 111,112 are made of a pressure sensitive, releasable adhesive, it becomes possible to dispense bags 102 from a stack thereof in which layer 111 abuts against a layer 112 of the bag above it in the stack, and layer 112 correspondingly abuts against a layer 111 of the bag beneath it. Layers 111,112 may also be offset from each other so that layers 111,112 of adjacent bags in the bag stack do not overlap each other, if problems with bag removal develop. Each layer 111,112 may also be made of two adhesive sublayers, including an outer layer of relatively weak, pressure sensitive releasable adhesive and an inner layer of a stronger (more tacky) adhesive which binds the outer layer to the associated bag face 108,109. This composite-type adhesive layer structure is useful in preventing unwanted transfer of the releaseable adhesive to an adhesive layer of an adjoining bag 102 in the bag stack.

The portion of backing 103 which extends beyond mouth 106 of bag 102 defines a flap 115 which is folded over an upper end portion of bag 102, including mouth 106 and front adhesive layer 111, so that the inner face of flap 115 engages and is releasably secured to front adhesive layer 111. Backing 103 may further have a pair of aligned, spaced-apart holes 116 which allow package 101 to hang from a hook or rod on a store shelf. Flap 115 is releasably secured to bag 102, and thereby allows the contents of the bag to be inspected and resealed by a potential purchaser. Resealable package 101 has wide applicability and could be used to store a wide variety of items, such as kit 100 as shown here.

As shown, both bag 102 and backing 103 preferably have a generally rectilinear shape for holding comparably shaped sheets. Bag 102 preferably has a width only slightly less than the width of backing 103, e.g. at least 9/10 the width of backing 103, but has a length substantially less than the length of backing 103, for example, no more than about ¾ or 4/5 the length of backing 103.

Figure 8:
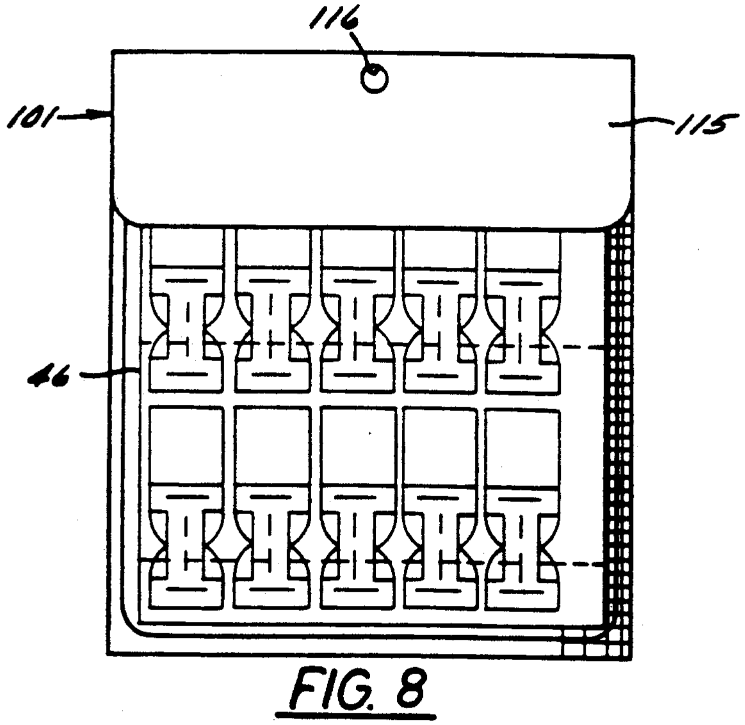
FIG. 8 is a front plan view of an indexing system according to the invention in packaged form.
Figure 9:
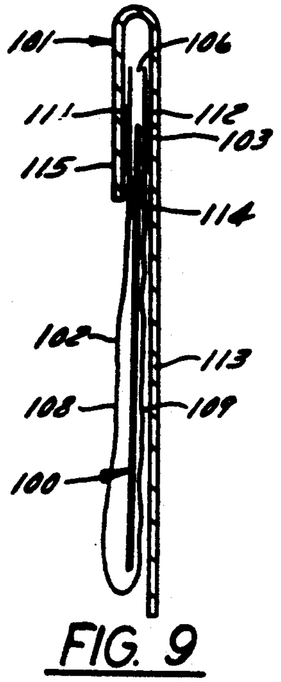
FIG. 9 is a lengthwise sectional view of the packaged indexing system shown in FIG. 8.
Figure 11:
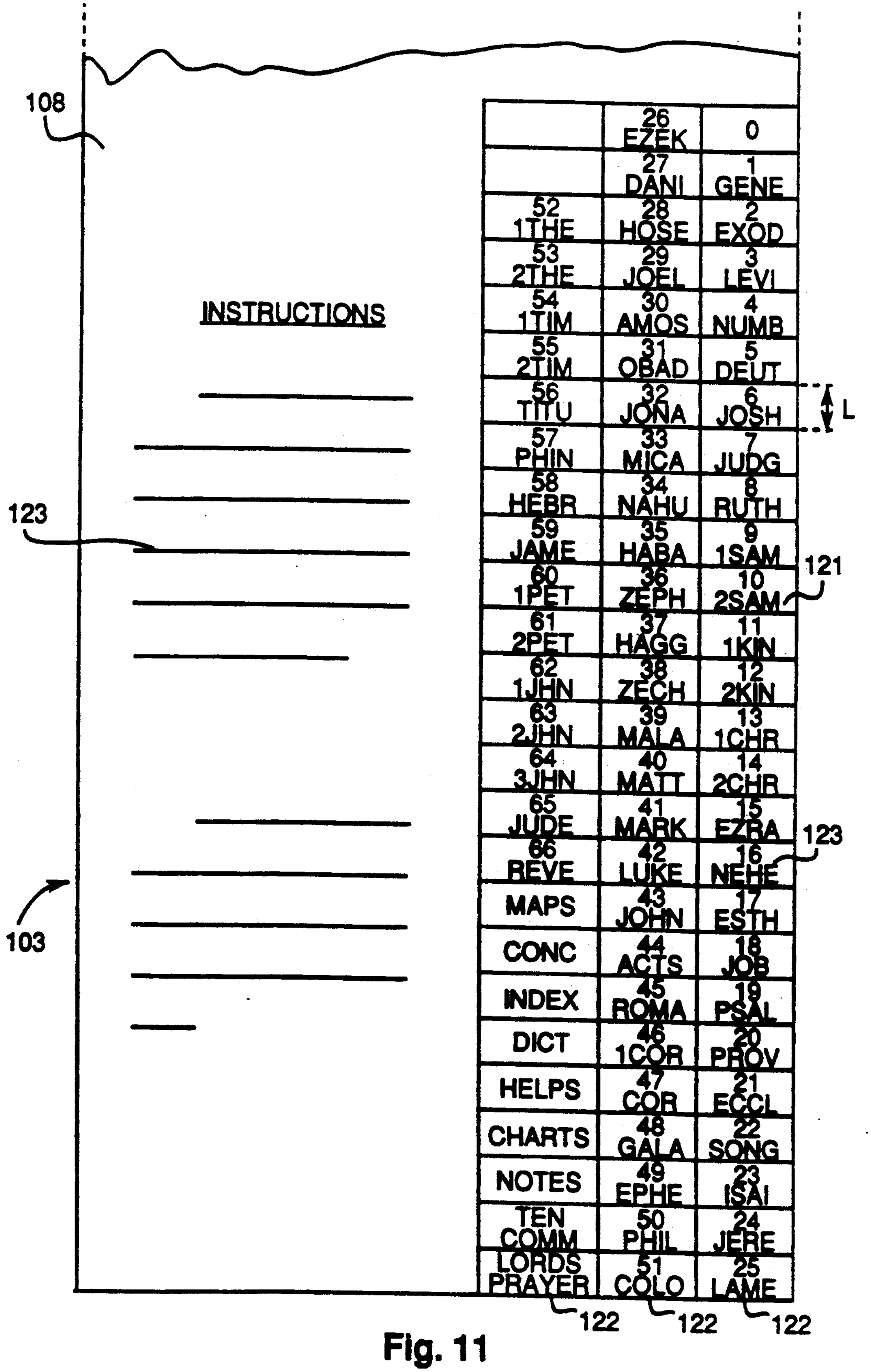
FIG. 11 is a partial front view of the backing card used in the packaged indexing system shown in FIG. 8.

Front face 108 of backing 103 additionally can provide the tab layout strip shown in FIG. 1. Referring to FIGS. 8 and 11, an array 120 of tab layout squares 121 is printed onto front face 108 at the lower right corner thereof, and extending if necessary the entire length of backing 103. In the alternative, a separate, preprinted folded layout strip may be included as part of the kit 100.

As shown in FIG. 11, each square 121 includes a number and has a length L that corresponds to the desired spacing for tabs 13 (compare FIGS. 2 and 11.) Each square 121 encloses indicia 123 including the appropriate tab number, and optionally the title (book name) for the tab or an abbreviation therefor. The sequence of numbered squares 121 along each column 122 matches the order in which tabs 13 are installed in bible 10.

Kit 100 is used as follows. The user opens package 101 and removes sheets 46, index table insert 11, and index table chart 12. A release paper backing (not shown) of insert 11 is removed, and insert 11 is permanently mounted in bible 10. The user then cuts up printed array 120 into individual strips (columns 122) and unites these strips end-to-end (as with adhesive tape) to make tab layout strip 14. Layout strip 14 consists of a single column of squares 121 disposed in numerical order. The user then holds layout strip 14 against his or her bible and determines the positions of each tab 13 in each row 81. Strip 14 is especially useful for determining where the last book, Revelations, falls, since this is the starting point for installing the tabs. For this purpose tabs 13 are set in descending numerical order on sheets 46 as shown in FIG. 6.

Kit 100 exemplifies numerous advantages of the indexing system according to the invention. Index table 11 or 12 provides a simple, fast system for locating a book in the bible when used in combination with numbered tabs 13. Sheet 46 for dispensing tabs 13 allows a user to dispense tabs or labels easily and in the correct order. Package 101 provides a simple, resealable package of wide utility.

The invention further provides an improved indexed book 10. Index table 11 can be preprinted into a book as part of the text in the manner of a normal index or table of contents. Similarly, tabs 13 can be built in in the manner of prior art permanent book tabs, such as by cut-away page edges or projections which extend from the outside margin of the first page of each book or chapter, as described in the patents cited above. To provide the tabbed pages with additional strength, it is especially preferred to employ thickened chapter pages in book 10. This is especially important where, as with bibles, very thin paper is employed for the text pages. The spaced-apart thickened pages correspond to biblical books, chapters or other subdivisions of the book, and should have a thickness of at least about twice the the thickness if the intervening pages. In this manner the present invention can be thereto later by means of kit 100.

The above description is of preferred exemplary embodiments of the invention, and the invention is not limited to the specific forms shown. For example, the indexing system according to the present invention is not limited to the bible. It can be advantageously designed for use with any book having numerous chapters or subparts often referred to by name. Similarly, the improved package according to the invention can be readily modified to hold a wide variety of objects, such as stationary, toys, household implements, foods, and other items normally sold in plastic bags. These and other modifications may be made in the design and arrangement of the invention without departing from the scope thereof as defined in the appended claims.

I claim:

1. A label dispensing sheet, comprising:

a backing sheet having a layer of a pressure sensitive adhesive releasing material on a face thereof and having a weakened line across the width thereof;

a row of labels releasably disposed on said backing sheet overlying said weakened line, each of said labels comprising a base layer having a layer of pressure sensitive adhesive coated on a bottom face thereof and disposed in face-to-face contact with said release layer of said backing sheet, and having indicia disposed on a top face thereof; and a release strip releasably disposed on said backing overlying said weakened line in said backing sheet, said strip having a layer of adhesive on a bottom face thereof in face-to-face contact with said release layer of said backing sheet, said release strip having a weakened line extending in the widthwise direction thereof at a position offset from said weakened line in said backing sheet.

2. The label dispensing sheet of claim 1, wherein said release strip is positioned at one end of said row of labels, and said weakened lines comprise generally parallel slits in said backing sheet and said release strip, respectively.

3. The label dispensing sheet of claim 1, wherein the base layer of each label comprises a thin, flexible, transparent film, and each label further comprises an intermediate layer bearing desired indicia disposed on the base layer, and a covering layer overlying the intermediate layer, which covering layer also comprises a thin, flexible transparent film.

4. The label dispensing sheet of claim 3, wherein said release strip is positioned at one end of said row of labels.

5. The label dispensing sheet of claim 4, wherein said base layer and said covering layer each have a thickness in the range of about 1 to 2 mils.

6. The label dispensing sheet of claim 5, wherein the transparent, flexible films of the base and covering layers each consist essentially of a polyester film.

7. The label dispensing sheet of claim 4, wherein the intermediate layer comprises a layer of ink or pigment.

8. The label dispensing sheet of claim 7, wherein the intermediate layer comprises a metallic ink sublayer printed with visible characters, the covering layer being effective to prevent tarnishing of the metallic ink.

9. The label dispensing sheet of claim 7, wherein the intermediate layer is generally H-shaped, including a central stem portion and a pair of parallel crossbar portions, and side edge portions of said base and covering layers taper inwardly and symmetrically in the lengthwise direction from both sides towards the center of said stem portion so that, at said center, the base and covering layers have the same width as the stem portion.

10. The label dispensing sheet of claim 9, wherein said side edge portions are curved, and said curved edge portions on opposite sides of said center of said stem align when said label is folded along said center to form an index tab.

11. The label dispensing sheet of claim 1, wherein the backing sheet further comprises a paper sheet, and the releasing material comprises silicone.

12. The label dispensing sheet of claim 3, wherein side edge portions of said base and covering layers taper inwardly and symmetrically in the lengthwise direction from both sides toward a widthwise centerline of said intermediate layer so that, at said centerline, the base and covering layers have the same width as the stem portion.

13. The label dispensing sheet of claim 12, wherein said side edge portions are curved, and said curved edge portions on opposite sides of said center of said stem align when said label is folded along said center to form an index tab.

* * * * *